United States Patent [19]
Worcel

[11] Patent Number: 5,993,450
[45] Date of Patent: Nov. 30, 1999

[54] OSTEOSYNTHESIS RING USABLE IN COMBINATION WITH A PIN OR A SCREW, AND COMPRESSING DEVICE THEREFORE

[76] Inventor: Alexandre Worcel, 36 rue de Pommard-F-75012, Paris, France

[21] Appl. No.: 08/973,198

[22] PCT Filed: Jun. 7, 1996

[86] PCT No.: PCT/FR96/00862

§ 371 Date: Dec. 3, 1997

§ 102(e) Date: Dec. 3, 1997

[87] PCT Pub. No.: WO96/39971

PCT Pub. Date: Dec. 19, 1996

[30] Foreign Application Priority Data

Jun. 7, 1995 [FR] France .................................... 95 06722

[51] Int. Cl.$^6$ ...................................................... A61B 17/56
[52] U.S. Cl. ................................ 606/73; 606/72; 606/59; 606/61
[58] Field of Search ................................ 606/72, 73, 59, 606/61, 60, 86

[56] References Cited

U.S. PATENT DOCUMENTS

| | | |
|---|---|---|
| 3,990,438 | 11/1976 | Pritchard . |
| 4,612,920 | 9/1986 | Lower . |
| 4,760,843 | 8/1988 | Fischer et al. . |
| 4,776,329 | 10/1988 | Treharne . |
| 4,790,304 | 12/1988 | Rosenberg . |
| 4,903,692 | 2/1990 | Reese . |
| 5,437,674 | 8/1995 | Worcel et al. . |

FOREIGN PATENT DOCUMENTS

| | | |
|---|---|---|
| 0 085 493A1 | 8/1983 | European Pat. Off. . |
| 0 209 685A2 | 1/1987 | European Pat. Off. . |
| 0 340 413A1 | 11/1989 | European Pat. Off. . |
| 0 630 613A2 | 12/1994 | European Pat. Off. . |
| 2 549 650A1 | 1/1985 | France . |
| 2 695 026A1 | 3/1994 | France . |

Primary Examiner—Michael Buiz
Assistant Examiner—Lie N Ngo
Attorney, Agent, or Firm—Burns, Doane, Swecker & Mathis, L.L.P.

[57] ABSTRACT

An osteosynthesis ring for maintaining one or more fractured bones in compression, the ring being used in combination with a pin, includes a hollow cylindrical body. The body is made of an elastic biocompatible material. The body has a channel extending therethrough along an axis of revolution of the body for receiving a pin. The body is structured for blocking at least one of translation and rotation of the body. A proximal part of the body includes a slot along at least one diameter of the body, the slot defining at least two separate parts, the at least two separate parts being adapted to spread apart from one another.

20 Claims, 4 Drawing Sheets

OSTEOSYNTHESIS RING USABLE IN COMBINATION WITH A PIN OR A SCREW, AND COMPRESSING DEVICE THEREFORE

BACKGROUND AND SUMMARY

The present invention relates to osteosynthesis devices, and more particularly to an improved ring which can be used in combination with a pin or a screw and is intended to maintain one or more fractured bones in compression, such as a bone of the hand or of the foot, and also to a device specially designed for compressing it.

Numerous devices intended to maintain two bones, or two bone fragments of a fractured bone, in compression have been described in the literature. For example, patent FR-A-2,549,650 describes an intra-medullary compression device which comprises a threaded rod bearing two opposite elements which each include disks for anchoring in the medullary cavity of the fractured bone, into which medullary cavity this device is introduced. The devices of this type are not suitable, however, for osteotomy of small bones.

U.S. Pat. No. 3,990,438 describes a fixation device for fractured bones comprising two parts, one of which has cutting threads which anchor in the main fragment of the bone, while the other part includes a thread cooperating with a screw, protruding from the bone, providing for the axial compression. This device cannot be used on bones of small dimension. Furthermore, the removal of the screw is very difficult on account of the osseous incarcerations which occur between the threads of the distal part of the screw and, in addition, the compression is not satisfactory.

Patent EP-A-085,493 describes a compression device comprising a self-tapping screw which engages in a sleeve, and the point of which fixes in the distal bone, as well as a blocking ring which is placed between the body of the screw and the sleeve.

Patent FR-A-2,695,026 describes a screw with fold-back wings integral with the proximal end of the screw, the head of which is hollow and can receive a cylindrical element acting on the free ends of the wings in order to fold them back. The whole arrangement can include an axial channel for the passage of a pin which is used for certain types of fractures.

Patent EP-A-0,209,685 describes a compression device formed by a screw which engages in a peg with a slotted head capable of fixing itself in the bone. This device has the disadvantage of being difficult to withdraw on account of the regrowth of bone which can block the peg.

These known devices are not generally designed for use in the reconstructive surgery of small bones, for example the bones of the foot and of the hand. Moreover, the head of the screw which is traditionally used stands out and forms a projection beyond the surface of the bone, and this entails serious risks of pain and of formation of seats of infection. This difficulty is eliminated in the screw known as the Herbert screw and formed by a headless compression screw, bearing on the two opposite cortical walls of the fractured bone or of the bone fragments, but the positioning of such a screw is a delicate operation.

Finally, it is generally imperative to prepare a very precise drill hole before putting into position the device for maintaining the fractured bone in compression, and this positioning, as well as the compression, are then often awkward to perform under good conditions.

The subject of the present invention is a novel osteosynthesis ring which is particularly designed for small bones, but may also be suitable for bones of large dimension, and which can be used in combination with a pin or a screw, and, where appropriate, an osteosynthesis plate.

Another subject of the invention is a device specially designed for the compression of such an osteosynthesis ring.

The osteosynthesis ring according to the present invention, for maintaining one or more fractured bones in compression, is intended to be used in combination with a pin or a screw, and, where appropriate, an osteosynthesis plate, and is of the type comprising a hollow cylindrical body; it is distinguished by the fact that:
  the body of the ring is made of an elastic biocompatible material,
  the body of the ring has a channel passing right through it along its axis of revolution and matching the pin,
  the body of the ring is equipped on its outer and/or inner part with a means for blocking in translation and/or in rotation,
  the proximal part of the body and/or the head of the ring is slotted along at least one diameter in order to form at least two separate parts which are capable of spreading apart from one another.

The means for blocking the osteosynthesis ring according to the invention can be formed by a spiral screw thread on the outer surface of the cylindrical body, cooperating, for example, with a tapped hole made in the osseous part where the ring is to be positioned. In one variant, the outer cylindrical surface is smooth, and the blocking means is formed by at least one flexible tongue, the free end of which will anchor itself in the osseous part or, preferably, in an osteosynthesis plate. In another variant, the blocking is achieved by fixation on the pin itself, and in this case the blocking means is provided on the inner face of the channel passing through the ring.

The osteosynthesis ring according to the invention is preferably formed by a headless screw, but it is possible to use headed screws of various forms.

According to a preferred embodiment, the osteosynthesis ring includes means for temporary attachment to the pin, which means can consist of a circular flange inside the axial channel.

As has been indicated hereinabove, the proximal part of the body and/or the head of the ring is divided into at least two parts by a diametral slot, or by two perpendicular slots, in this case forming a cruciform recess.

This diametral slot can advantageously have a beveled section over part or all of the diameter, facilitating the positioning of the ring, in combination with an apparatus or ancillary device of the type described hereinafter. Moreover, the ring can also include a transverse slot, in a plane perpendicular to the axis of the ring, and passing through the latter along approximately half its diameter, preferably in its distal part, near its central part.

The osteosynthesis ring according to the invention is made of any biocompatible material having satisfactory mechanical properties, and for example of treated steel, stainless steel, steel having a high nitrogen content, an alloy based on titanium, aluminum and vanadium or molybdenum, such as TA6V or TA6M alloys, and in a general manner all the metals corresponding to the standard ISO 5832.

The osteosynthesis ring according to the present invention affords several advantages compared to the conventional devices used in the art.

As in the case of the Herbert screw, it does not form a protrusion at the bone surface, and, moreover, its positioning is made easy because it is guided by the pin. In addition, the same osteosynthesis ring can be used in situations where conventional screws of different sizes would have to be employed.

Furthermore, in the case of an osteosynthesis screw, it is no longer necessary to prepare a drill hole specially designed for the screw, and the positioning of the screw according to the invention is made easier. Consequently, the risks of loss of the reduction of the fracture during the osteosynthesis are greatly reduced.

The production of the ring according to the present invention is simple and relatively inexpensive, since it is not necessary to carry out a delicate operation of perforation for a screw of very small dimension, in contrast to the well known Herbert screw which is poorly adapted to osteosynthesis of the small bones of the foot and of the hand.

The positioning of the ring according to the invention can advantageously be effected using a dynamometric compression device, which greatly limits the risks of excessive traction leading to extraction of the fixation thread of the screw or of the pin from the cortical bone during compression of the fractured bone.

In the case of surgery of the foot, and, especially, of the hand, the ring of the invention, used in the variant of the ring with an external spiral thread, combined with a pin on which it is fixed, permits osteosynthesis of the small bones of the hand to be carried out with greater ease and improved efficacy compared to the conventional techniques, which entail a substantial risk of loss of reduction of the fracture.

In one variant according to the present invention, the ring is associated with a pin including a so-called "distal cancellous" thread and a polygonal cross section, for example hexagonal, permitting the osteosynthesis of fractures of the scaphoid bone, with a possibility of dynamometric compression, avoiding the risks of extraction from the cancellous bone in the distal part.

The invention also extends to an ancillary device specially designed for the compression of an osteosynthesis ring such as has been described hereinabove.

The ancillary device for compression of a fractured bone, using a ring according to the invention, comprises at least two coaxial cylinders which can slide one inside the other along their axis and are connected by a spring, one of the cylinders including means for temporary attachment to the pin or the screw passing through the ring.

The spring is a preset dynamometric spring which can be compressed prior to the positioning of the ring and the compression of the fractured bone.

In a variant designed for a ring fixed on a pin, one of the cylinders comprises, at its free end, means for holding the ring during its positioning, and the other cylinder is provided with a collar or a mandrel for clamping on the pin.

In a second variant designed for a ring fixed on a screw rod associated with an osteosynthesis plate, the ancillary device includes an intermediate cylindrical tube including means for fixing to the plate, for example a screw thread cooperating with a tapped hole provided in the plate.

In a general manner, the ring according to the present invention, combined with a pin and/or a plate, can be employed in all applications where use is made of lost pins, that is to say pins which are left in place after the surgical intervention.

Thus, it can be used in osteosynthesis of fractures of the tibial plateaus, where the characteristics of the ring prevent the pin from migrating. Moreover, the pin can be cut flush with the surface of the bone and no longer protrudes under the skin. This reduces the risks of pain and infection.

The ring of the invention can also be employed in the osteosynthesis of osteochondral fractures of the lower end of the femur, as well as of the astragalus, where the use of the ring in arthroscopy is made easier by the fact that the specially designed ancillary positioning device forms, together with the ring, an assembly which it is easy for the surgeon to manipulate.

In the case of fractures of the wrist, it is possible to use the technique of styloid pinning, and the absence of a protrusion of the pin avoids the risk of tendon rupture on the pin and of infection on the pin, very common in the conventional techniques. Moreover, the lifetime of the osteo-synthesis is distinctly improved by virtue of the good implantation of the pin held by the screw, or the ring, which prevents it from migrating.

The osteosynthesis ring according to the invention can also be used for the reduction of fractures of the neck of the femur, in the same way as in the case of fractures of the scaphoid bone, by giving the twin advantage, compared to the conventional techniques, of great simplicity of positioning and the possibility of dynamometric compression.

In accordance with the present invention, the positioning is carried out in the following manner, more particularly in the case of the variant consisting of a ring with an external screw thread. Once the fracture has been reduced and is being held by a pin, for example a notched pin, the first cortical bone is hollowed out slightly using a suitable instrument, for example a perforated square point. The ring is then mounted on the screwdriver, the effect of which is to spread open the upper parts of the ring by distancing them from one another, and the assembly is engaged on the part of the pin protruding from the bone. The ring is then screwed until it is flush with the surface of the bone, and then the screwdriver is removed.

By virtue of the elasticity of the material used, the upper parts of the ring are drawn together, and the ring is thus blocked on the pin. The form given to the means of attachment of the ring and of the pin makes it possible to obtain a unidirectional or bidirectional blocking in translation, depending on the result which is sought.

The same operation is performed on the opposite cortical bone.

The compression is then carried out on one or other of the two sides, if desired, by means of the ancillary device for dynamometric compression. It then suffices to cut the protruding ends of the pins flush with the rings.

In one variant according to the invention including a pin with a distal threading which can anchor in the opposite cortical bone, this pin is used as a conventional screw, then the ring according to the invention is engaged on the pin, compressed and blocked on the pin as indicated hereinabove.

The pin can have a polygonal cross section and have a male head, in which case a screwdriver with a female head is used.

In the case of a ring according to the invention combined with an osteosynthesis plate, the positioning can be carried out as is described in greater detail hereinafter.

BRIEF DESCRIPTION OF THE DRAWINGS

The following examples illustrate the invention in greater detail without limiting its scope, with reference

Figure 1:
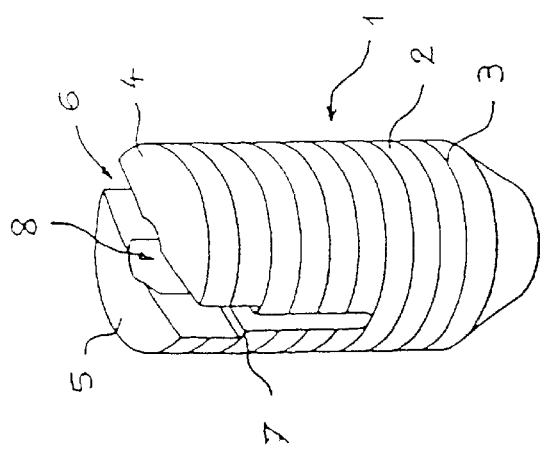
FIG. 1 is a perspective view of an osteosynthesis ring according to an embodiment of the present invention.

The screw (1) represented in FIG. 1 is made of a material of suitable flexibility and elasticity, for example stainless steel or an alloy such as TA6V (titanium, aluminum and vanadium alloy) or TA6M (titanium, aluminum and molybdenum alloy). It is of cylindro-conical shape with a cylindrical body (2) which has a spiral screw thread (3) over all of its external surface. This screw thread can be of the cancellous bone type or cortical bone type.

The proximal part of the body (2) of the screw is separated into two parts (4) and (5) by a slot (6) formed in a diametral plane. The cross section of the slot (6) includes a shoulder (7) delimiting two parts, the one situated toward the head of the screw being wider and corresponding substantially to the thickness of the edge of the blade of the screwdriver used for screwing.

Figure 2:
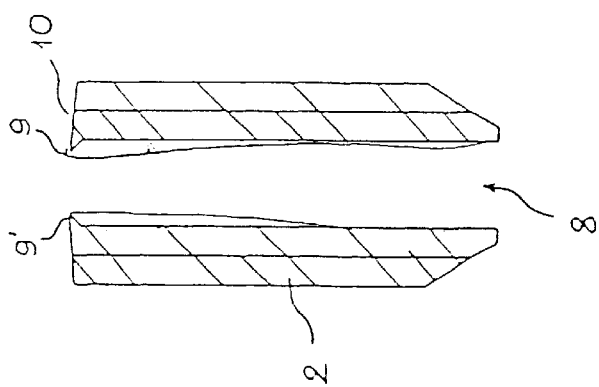
FIG. 2 is a cross-section through the ring in FIG. 1 on a diametral plane.

As is shown in FIG. 2, the body (2) of the screw has a channel (8) passing right through it and situated on its axis. In the embodiment represented in FIG. 2, this channel (8) includes two circular flange segments (9, 9') forming a narrowing at the level of the upper surface (10) constituting the head of the screw. These flange segments (9), of beveled shape, will be applied against the surface of the pin passing through the screw (1) via the axial channel (8). The diameter of the pin being slightly smaller than the internal diameter of the channel (8) in the body (2) of the screw, the two parts (4) and (5) of the body of the screw are spread slightly apart from one another and the compression effect resulting from the elasticity of the material reinforces the contact of the internal edge of the flange (9) against the surface of the pin and provides a blocking effect.

The beveled shape of the edge of the flange (9) in this case creates a unidirectional blocking. Of course, the direction of the blocking is controlled by the shape of the bevel. By using the edge of a flange (9) in the form of a point with a symmetrical triangular cross section, a bidirectional blocking is achieved.

Figure 3:
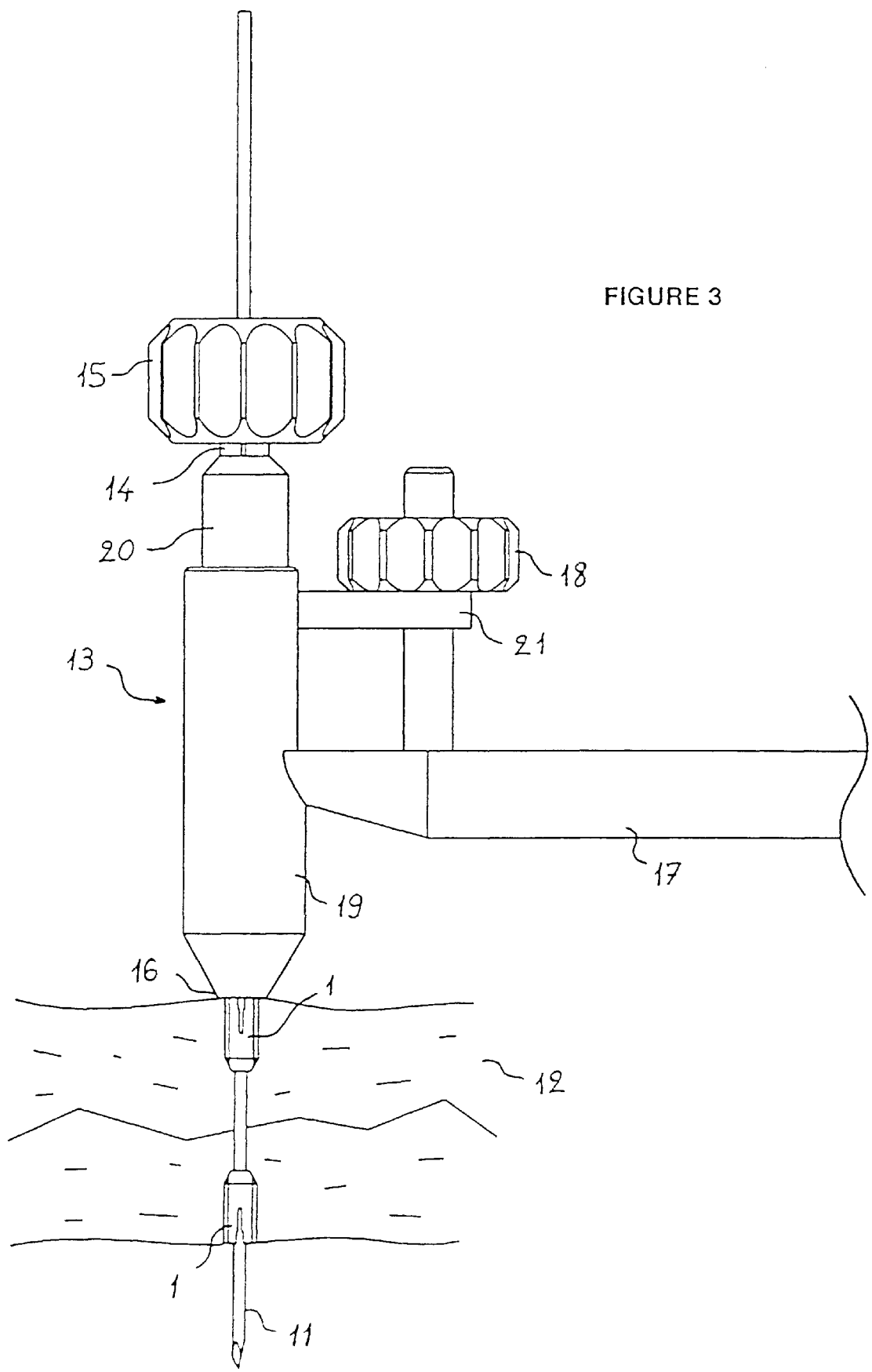
FIG. 3 is an elevation view of an ancillary device for compressing the rind according to an embodiment of the invention.

The ancillary device represented in FIG. 3 is especially intended for compressing a fractured bone (12) by means of the screw (1) on the pin (11) passing through the fractured bone (12).

In the arrangement in FIG. 3, the pin (11) and two screws (1) are put in place, the ancillary device being represented on the pin in order to make it easier to understand.

The ancillary device (13) includes a mandrel (14) which holds the pin (11) and can be blocked by a nut (15). The screw (1), engaged on the pin (11), is simply held in position on the point (16) of the ancillary device opposite the mandrel (14) by a single spring (not shown in this figure).

The ancillary device is used in the following way. The pin first having been put into place through the bone fragments using a conventional technique, the screw (1) is placed on the point of a screwdriver of suitable shape (not shown), the blade of which has a thickness slightly greater than the width of the slot (6) in order to push back and spread open the two parts (4) and (5) of the screw. The screw is then engaged on the part of the pin emerging from the bone, and it is screwed until it is flush with the surface of the bone. In this position, no compression has yet been exerted.

When the screwdriver is removed, the two parts (4) and (5) are freed and come to bear on the pin (11) which is then blocked by the pressure exerted by the flange segments (9) and (9') shown in FIG. 2. The same operation is repeated to put the second screw (1) into place on the other face of the bone, and the pin is thus blocked on its two ends protruding from either side of the fractured bone.

The nut (18) of the ancillary device (13), held by hand via the grip (17) integral with the body (19) of the ancillary device, is then screwed counter to the pressure of a spring (not shown) situated inside the body (19). The effect of this screwing is to cause the cylindrical part (20) to penetrate into the body (19) of the ancillary device and to compress the internal spring. Dynamometric pressure measurement graduations are marked on the wall of the cylindrical part (20) to make it easier for the practitioner to regulate.

This ancillary device (13), preset in this way, is engaged on the pin (11) until the point (16) is situated in contact with the screw (1). By then acting on the nut (15), the mandrel (14) is blocked on the pin (11) and the ancillary device is immobilized. The second nut (18) is then acted upon in the direction of unscrewing, in order to release the force exerted by the spring. The nut (18) keeps the arm (21) integral with the cylindrical part (20) (of which only the upper part is shown in FIG. 3) blocked on the pin (11) by way of the mandrel (14). The body (19) then slides on the pin (11) under the pressure of the internal spring and pushes the ring (1) back, the blocking of the ring being unidirectional, and compresses the fractured bone.

The nut (15) is then unscrewed in order to unblock the ancillary device from the pin (11) and to remove it. In the embodiment represented in FIG. 3, in order to facilitate comprehension, the pin (11) includes a rod emerging from the bone by a substantial length, passing completely through the ancillary device. Of course, in practice it suffices for the pin to protrude by a length enabling it to be gripped by the ancillary device.

Figure 4:
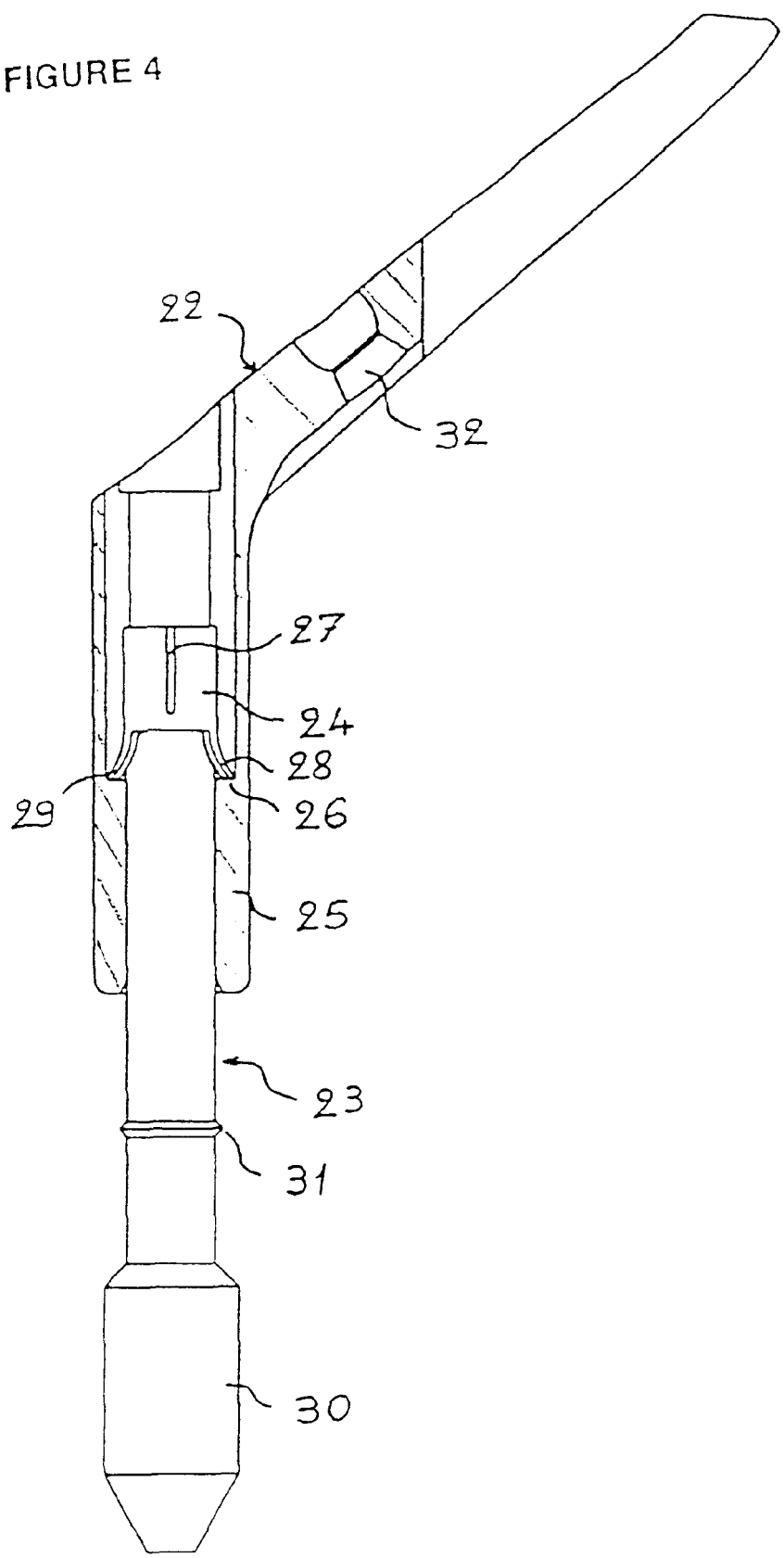
FIG. 4 is a cutaway view of a screw/ring/plate assembly.

The dynamometric device indicated hereinabove, avoiding excessive stresses, is of the usual type. FIG. 4 shows a partial cutaway view of an osteosynthesis plate (22) associated with a screw/pin (23) for fixation, combined with a ring according to the invention.

The blocking ring (24) of the invention is placed on the head of the pin/screw (23), of which the rod is held tight in the barrel (25) of the plate (22). The latter is divided into two parts, the upper part having an internal diameter slightly greater than the lower part, the junction between the two parts thus forming a shoulder (26).

The ring (24) has a slot (27) substantially in a diametral plane, and two tongues (28) and (29) for blocking against the inner wall of the barrel (25) on the shoulder (26).

A distal thread is provided on the cylindrical wall of the point (30) of the screw (23) in order to ensure the anchoring in the osseous part. A ring (31) is formed at the surface of the body of the screw (23) to serve as an abutment cooperating with the lower edge of the barrel (25). The upper end of the body of the screw (23) protruding slightly above the shoulder (26) in the barrel (25) bears a linear or cruciform recess in order to permit screwing via a normal ancillary device of the screwdriver type.

The plate (22) also includes several orifices, of which only one (32) is shown, for fixation on the surface of the fractured bone by means of normal screws. This device is very particularly suitable for fractures of the neck of the femur. Its positioning and its compression are explained below.

Figure 5:
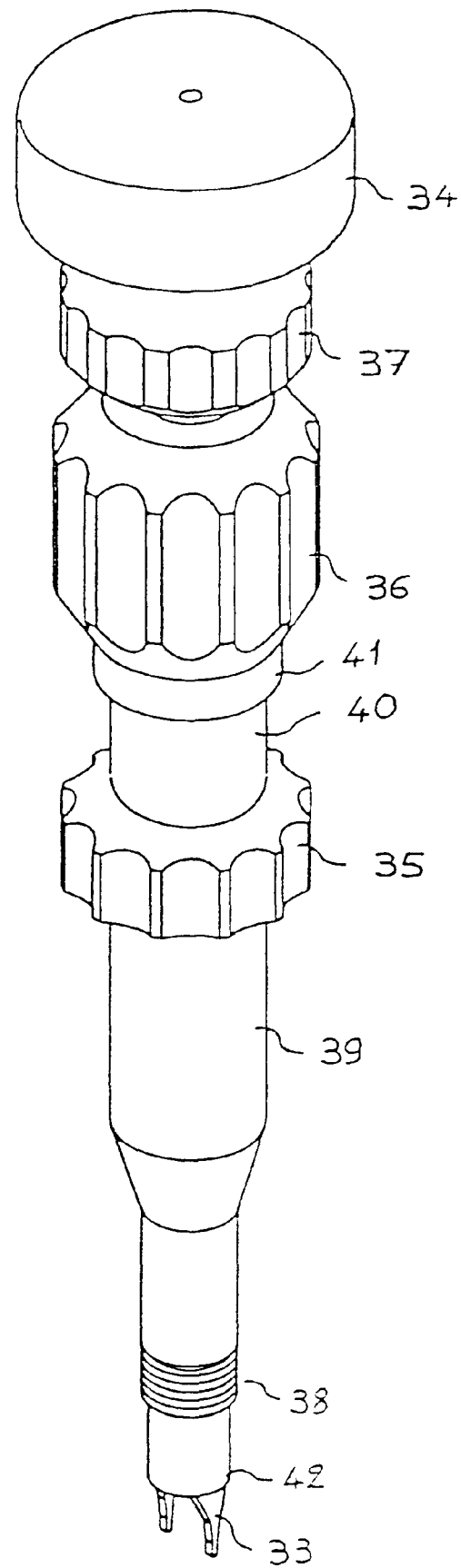
FIG. 5 is a perspective view of another ancillary device designed for positioning the ring.

The ancillary device shown in FIG. 5 is very particularly intended for the compression of the device in FIG. 4.

It includes a recessed point (33) and, at the opposite end, a handle (34). It also comprises three knurled control wheels (35), (36) and (37).

The knurled wheel (35) is integral with the cylinder (39) surrounding the rod and the head (33) of the screwdriver, and bearing the spiral screw thread (38) intended for temporary fixation of the ancillary device in the osteosynthesis plate, upon positioning of the ring and compression of the fractured bone.

The knurled wheel (36) is screwed onto the cylinder (40) bearing graduations, which is integral with the cylinder (39). By acting on the knurled wheel (36) in the direction of screwing counter to the action of an internal spring (not shown), the rod of the screwdriver is advanced into the cylinder (39), and the base of the cylinder (41), integral with the knurled wheel (36), in combination with the graduations marked on the cylinder (40), permits precise adjustment. In this movement, the ring (24) according to the invention is pushed back by the end of the cylindrical piece (42).

The knurled wheel (37) makes it possible to act on the rod of the screwdriver, which can slide in the cylindrical piece (42).

In accordance with the present invention, the plate in FIG. 4 is used in the following way.

The osseous part which is to receive the screw/pin for fixation is firstly drilled using conventional techniques. The screw/pin (23) is then joined to the plate (22) by introducing the body of the screw into the barrel (25) of the plate until the upper end of the body of the screw protrudes slightly above the shoulder (26) in the barrel (25). The point of an ancillary positioning device is then introduced through the upper orifice of the barrel (25), and, the three elements—screw, plate, ancillary device—being held together, the point of the screw is inserted into the hole previously drilled in the osseous part, and then screwing is carried out by means of the ancillary device acting on the screw (23) until the plate (22) is in contact with the fractured bone. The usual screws are then placed in the orifices (32) of the plate (22).

The ancillary compression device shown in FIG. 5 is then used to block the rotation of the main screw (23) by means of the blocking ring (24). For this purpose, the point of the ancillary device is engaged in the slot (27), the effect of which is to spread apart the two upper parts of the ring, and the ring is engaged on the upper part of the body of the screw. In this movement, the point of each of the two tongues (28) and (29) slides against the inner wall of the upper part of the barrel (25). Where appropriate, guide grooves can be provided in the wall of the barrel in order to make positioning of the ring easier.

By acting on the knurled wheel (35), the ancillary device is fixed temporarily to the plate by means of the screw thread (38) cooperating with a tapped hole provided in the opening of the orifice of the barrel (25) of the plate (22). By then acting on the second knurled wheel (36), in the direction of screwing, the ring (24) is pushed back into the barrel (25) counter to the force of the internal spring of the ancillary device, acting as a dynamometric control spring.

By then acting on the third knurled wheel (37), in the direction of screwing, and with the ancillary device still being fixed in the plate by the screw thread (38), the point (33) of the ancillary device is caused to withdraw from the slot (27) and the two upper parts of the ring (25) are drawn against the main screw (23), while the free ends of the tongues (28) and (29) anchor in the inner wall of the barrel (25), thereby ensuring the blocking of the main screw (23).

Finally, in a last step, the knurled wheel (35) is unscrewed in order to release the ancillary device from the plate (22).

It has thus been possible to place the ring (24) in the barrel (25) of the plate (22) in order to block the screw (23) and compress the bone, with maximum safety by virtue of the presetting of the dynamometric spring of the ancillary compression device.

Figure 6:
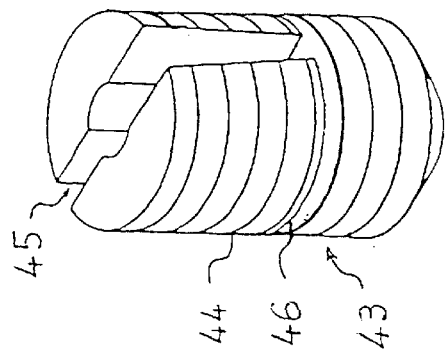
FIG. 6 is a perspective view of a variant of the osteosynthesis ring according to an embodiment of the present invention.

The variant of the osteosynthesis ring which is shown in FIG. 6 represents a refined form of the ring in FIG. 1. This ring is in the form of a screw (43) made of stainless steel or of an alloy having suitable properties of flexibility and elasticity, and it has a spiral screw thread (44) over the whole of its external surface.

The proximal part of the body of the screw (43) includes a diametral slot (45) beveled over only half of its width. FIG. 6 shows the bevel provided on one of the two thicknesses of the screw traversed by the slot (45).

Moreover, the screw includes a second slot (46) in a transverse plane perpendicular to the axis of the screw (43), in the distal part of the body of the screw, near its central part. The depth of this transverse slot (46) is slightly greater than half the diameter of the screw (43).

This particular form makes it possible to obtain a suitable flexibility and facilitates positioning using a blade which is itself beveled, such as the point (33) of the ancillary device in FIG. 5.

I claim:

1. An osteosynthesis ring for maintaining one or more fractured bones in compression, the ring being used in combination with a pin, comprising:

a hollow cylindrical body the body being made of an elastic biocompatible material, the body having a channel extending therethrough along an axis of revolution of the body for receiving a pin, the body having means for blocking at least one of translation and rotation of the body, and a proximal part of the body including a slot along at least one diameter of the body, the slot defining at least two separate parts, the at least two separate parts being adapted to spread apart from one another, wherein the an inner surface of the channel includes a flange for attachment to the pin.

2. The osteosynthesis ring according to claim 1, wherein the blocking means includes a spiral screw thread on an outer surface of the body.

3. The osteosynthesis ring according to claim 1, wherein the blocking means includes at least one flexible tongue, the at least one tongue having a free end adapted to anchor itself in a member.

4. The osteosynthesis ring according to claim 1, further comprising means for temporary attachment of the body to the pin.

5. An osteosynthesis ring for maintaining one or more fractured bones in compression, the ring being used in combination with a pin, comprising:

a hollow cylindrical body the body being made of an elastic biocompatible material, the body having a channel extending therethrough along an axis of revolution of the body for receiving a pin, the body having means for blocking at least one of translation and rotation of the body, and a proximal part of the body including a slot along at least one diameter of the body, the slot defining at least two separate parts, the at least two separate parts being adapted to spread apart from one another, means for attachment of the body to the pin, wherein the means for attachment between the screw and the pin includes a circular flange inside the channel.

6. The osteosynthesis ring according to claim 1, wherein the body is formed from a headless screw.

7. An osteosynthesis ring for maintaining one or more fractured bones in compression, the ring being used in combination with a pin, comprising:

a hollow cylindrical body the body being made of an elastic biocompatible material, the body having a channel extending therethrough along an axis of revolution of the body for receiving a pin, the body having means for blocking at least one of translation and rotation of the body, and a proximal part of the body including a slot along at least one diameter of the body, the slot defining at least two separate parts, the at least two separate parts being adapted to spread apart from one another, wherein the slot includes a beveled section over at least part of a diameter of the body.

8. The osteosynthesis ring according to claim 1, wherein the body further includes includes a transverse slot, the transverse slot being disposed in a plane perpendicular to the axis of revolution of the body, and the transverse slot extending through the body along approximately half of the diameter of the body.

9. An arrangement for compression of a fractured bone, comprising:

a pin;

an osteosynthesis ring for maintaining one or more fractured bones in compression, the ring being used in combination with a pin, the ring including a hollow cylindrical body the body being made of an elastic biocompatible material, the body having a channel extending therethrough along an axis of revolution of the body, the pin being received in the channel, the body having means for blocking at least one of translation and rotation of the body, and a proximal part of the body including a slot along at least one diameter of the body, the slot defining at least two separate parts, the at least two separate parts being adapted to spread apart from one another;

at least two, telescoping, coaxial cylinders, the at least two cylinders being connected by a spring, one of the at least two cylinders including means for temporary attachment to the pin recieved in the channel.

10. The arrangement according to claim 9, wherein a first one of the at least two cylinders, at a free end thereof, means for holding the ring, and a second one of the at least two cylinders includes a collar for clamping on the pin.

11. The arrangement according to claim 9, wherein the at least two cylinders includes an intermediate cylindrical tube, the intermediate tube including means for fixing the intermediate tube to an osteosynthesis plate.

12. The osteosynthesis ring according to claim 5, wherein the blocking means includes a spiral screw thread on an outer surface of the body.

13. The osteosynthesis ring according to claim 5, wherein the blocking means includes at least one flexible tongue, the at least one tongue having a free end adapted to anchor itself in a member.

14. The osteosynthesis ring according to claim 5, wherein the slot includes a beveled section over at least part of a diameter of the body.

15. The osteosynthesis ring according to claim 5, wherein the body further includes a transverse slot, the transverse slot being disposed in a plane perpendicular to the axis of revolution of the body, and the transverse slot extending through the body along approximately half of the diameter of the body.

16. The osteosynthesis ring according to claim 7, wherein the blocking means includes a spiral screw thread on an outer surface of the body.

17. The osteosynthesis ring according to claim 7, wherein the blocking means includes at least one flexible tongue, the at least one tongue having a free end adapted to anchor itself in a member.

18. The osteosynthesis ring according to claim 7, wherein the slot includes a beveled section over at least part of a diameter of the body.

19. The osteosynthesis ring according to claim 7, wherein the body further includes a transverse slot, the transverse slot being disposed in a plane perpendicular to the axis of revolution of the body, and the transverse slot extending through the body along approximately half of the diameter of the body.

20. The osteosynthesis ring according to claim 7, further comprising means for temporary attachment of the body to the pin.

\* \* \* \* \*